United States Patent [19]
Yamashita et al.

[11] Patent Number: 5,090,415
[45] Date of Patent: Feb. 25, 1992

[54] EXAMINATION APPARATUS

[75] Inventors: Takaji Yamashita; Yutaka Yamashita, both of Shizuoka, Japan

[73] Assignee: Hamamatsu Photonics Kabushiki Kaisha, Shizuoka, Japan

[21] Appl. No.: 639,377

[22] Filed: Jan. 11, 1991

Related U.S. Application Data

[63] Continuation of Ser. No. 310,176, Feb. 14, 1989, abandoned.

[51] Int. Cl.$^5$ ................................................ A61B 5/00
[52] U.S. Cl. .................................................. 128/665
[58] Field of Search ........................ 128/633, 634, 665

[56] References Cited

U.S. PATENT DOCUMENTS

| | | | |
|---|---|---|---|
| 4,018,534 | 4/1977 | Thorn et al. | 356/201 |
| 4,207,892 | 6/1980 | Binder | 128/665 |
| 4,281,645 | 8/1981 | Jobsis | 128/633 |
| 4,515,165 | 5/1985 | Carroll | 128/664 |
| 4,655,225 | 4/1987 | Dühne et al. | 128/664 |

Primary Examiner—Francis Jaworski
Attorney, Agent, or Firm—Finnegan, Henderson, Farabow, Garrett, and Dunner

[57] ABSTRACT

An examination apparatus for examining with transmission photometry an object of interest. The apparatus comprises: light launching means for successively launching an incidence light beam to the object at an incidence site; and light pickup means for picking up, in synchronism with launching of the incidence light beam, light beams scattered in the object from a plurality of output sites as light intensity data, and performing mathematical processing on the light intensity data for every launching of said incidence light beam to obtain absorption data representing a light absorption quantity at the incidence site.

7 Claims, 3 Drawing Sheets

EXAMINATION APPARATUS

This application is a continuation, of now abandoned application Ser. No. 07/310,176, filed Feb. 14, 1989, and now abandoned.

BACKGROUND OF THE INVENTION

The present invention relates to an apparatus for examining a certain abnormality in an object to be measured, such as a disease in the brain, by making use of light.

Apparatus are known that examine diseases in various body organs such as the brain by making use of light. FIG. 5 illustrates an application of the examination apparatus disclosed in U.S. Pat. No. 4,281,645. As shown, a plurality of light launching fibers $L_1$-$L_6$ for guiding light beams emitted from the corresponding number of light sources and a plurality of light pickup fibers $S_1$-$S_6$ that are associated with the fibers $L_1$-$L_6$ are attached to the head. The pickup fibers $S_1$-$S_6$ are located on positions that are opposite to those of the associated launching fibers $L_1$-$L_6$ in such a way that near infrared light beams launched into the head through fibers $L_1$-$L_6$ will be guided to a photodetector for detecting the quantity of light that has been transmitted through the head.

In the apparatus shown in FIG. 5, near infrared light beams are sequentially launched from fibers $L_1$-$L_6$, and the quantities of light that are transmitted through the head and emerge from the pickup fibers $S_1$-$S_6$ that are associated with the fibers $L_1$-$L_6$ are sequentially detected with the photodetector. On the basis of the quantities of transmission light that have been guided by the pickup fibers $S_1$-$S_6$ and detected by the photodetector, the absorption of near infrared light by hemoglobin in the brain is calculated to determine the temporal or time-dependent change in cerebral blood flow and the oxygen saturation in blood. This enables the measurement of light absorption at various sites in the brain on the straight lines that connect the launching fibers $L_1$-$L_6$ and the pickup fibers $S_1$-$S_6$.

As described above, the light launching fibers $L_1$-$L_6$ in the prior art examination apparatus correspond in a one-to-one relationship to the light pickup fibers $S_1$-$S_6$. Therefore, in order to achieve high-sensitivity detection of the light absorbance at sites in the brain on the straight line that connects a certain launching fiber, Say, $L_1$ and the corresponding pickup fiber, say, $S_1$, the amount of light emitted from the light source connected to the launching fiber $L_1$ has to be increased. As a further problem, the prior art apparatus is not suitable for precise detection because the slight shift in the directions or positions of the fibers $L_1$ and $S_1$ will cause a great variation in the result of detection. There is also a problem that in the brain the direction of light travel is considerably disturbed by scattering.

SUMMARY OF THE INVENTION

An object, therefore, of the present invention is to provide an examination apparatus that does not require very strong light to be emitted from a light source for achieving high-sensitivity detection of information on a local site in an object to be measured.

Another object of the present invention is to provide an examination apparatus that ensures precise detection without being substantially influenced by a shift in the position or direction in which optical fibers are attached to the object to be measured.

These objects of the present invention can be attained by an examination apparatus that comprises: light launching means by which light is launched into an object to be measured; and light pickup means by which light beams scattered in the object to be measured are picked up from a plurality of sites and processed and which is adapted to perform mathematical processing on intensities of picked-up scattered light beams.

In the present invention, light is launched into a selected site in the object to be measured and light beams scattered in the object are picked up from a plurality of sites in the object simultaneously to be subjected to a mathematical processing such as arithmetic addition. The intensity of scattered light that has been obtained as a result of arithmetic addition is proportional to the light transmittance of the incident site and hence can be used as a basis for determining the light absorption at a local site, that is, the incident site.

DETAILED DESCRIPTION OF THE PREFERRED EMBODIMENT

An embodiment of the present invention will be described hereinafter with reference to the accompanying drawings.

Figure 1:
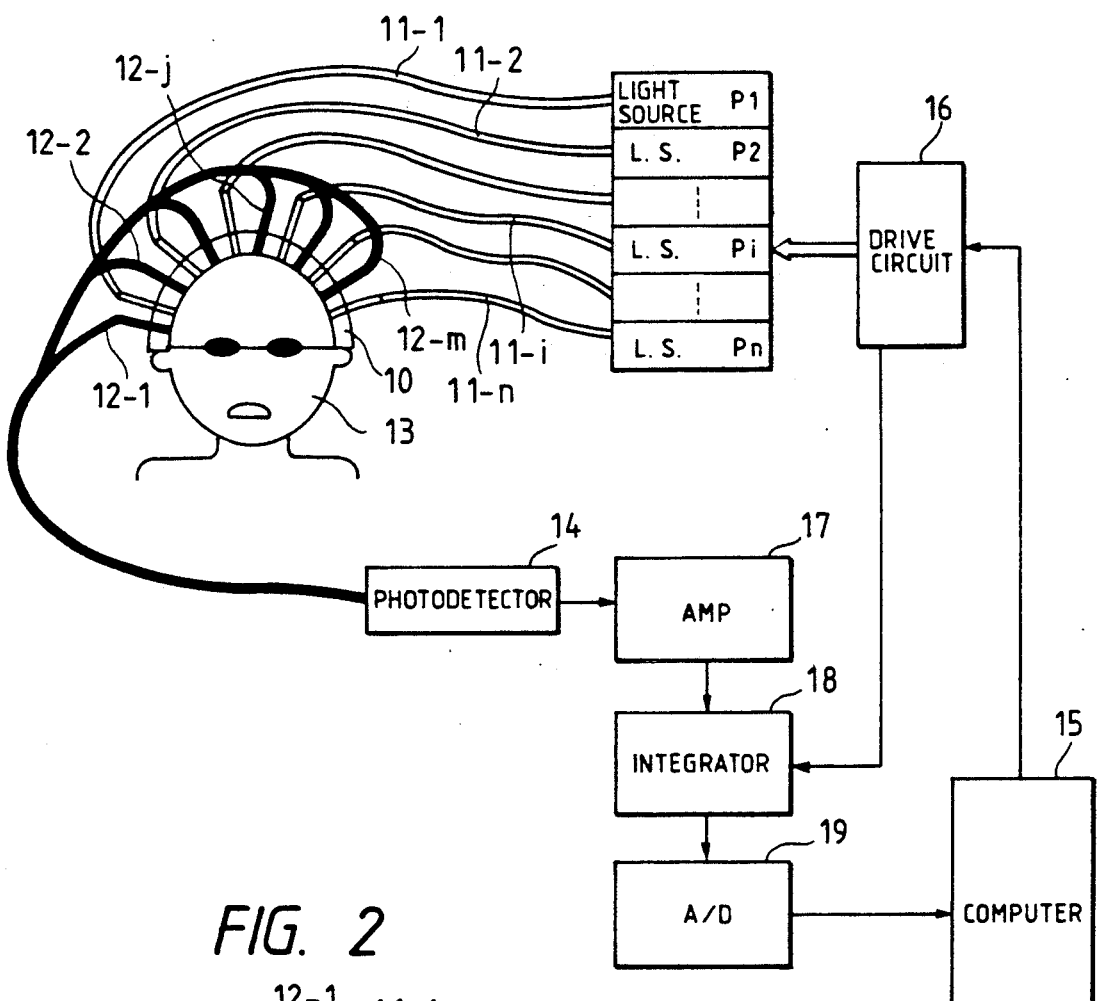
FIG. 1 is a schematic diagram showing the constitution of an examination apparatus according to an embodiment of the present invention.
Figure 2:
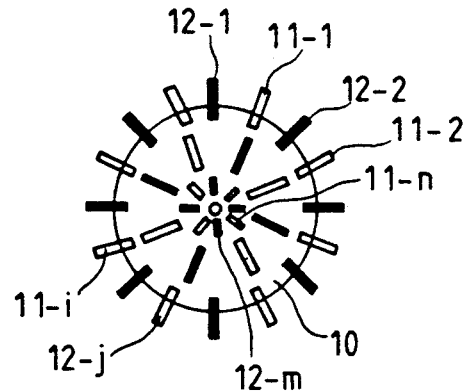
FIG. 2 is a plan view of a cap in helmet form.
Figure 3:
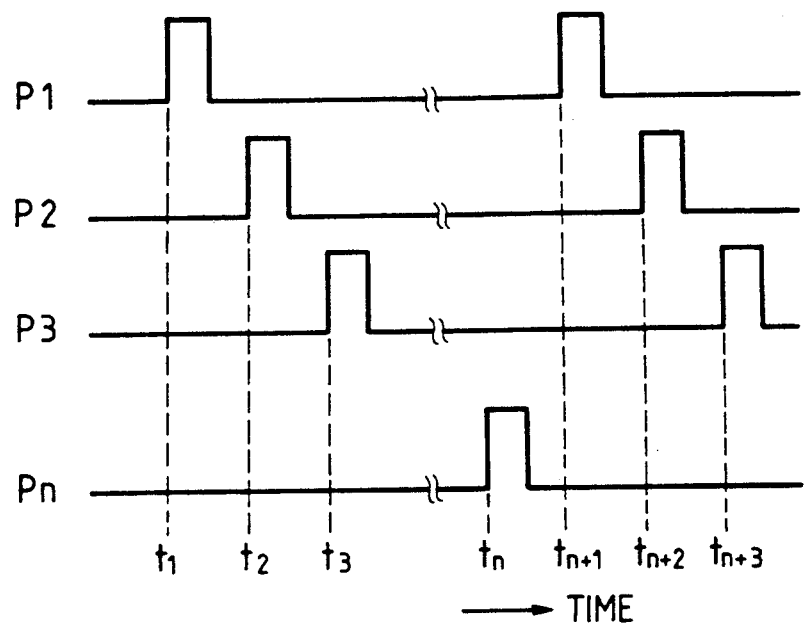
FIG. 3 is a timing chart for the driving of a plurality of light sources.

FIG. 1 is a schematic diagram of an examination apparatus according to one embodiment of the present invention. FIG. 2 is a plan view of a cap in helmet form. As shown in FIGS. 1 and 2, a helmet-like cap 10 has a plurality of light launching fibers 11-$l$ to 11-$n$ and a plurality of light pickup fibers 12-$l$ to 12-$m$ that are attached to the cap in such a way that they surround uniformly an object to be measured, say a head 13. These fibers are attached in such a way that their tips are located either in contact with the head 13 or in its vicinity when the cap 10 is put on the head 13.

The launching fibers 11-$l$ to 11-$n$ are connected at the other ends to associated pulse light sources, such as laser diodes, P$l$ to P$n$. The pickup fibers 12-$l$ to 12-$m$ are held together in a bundle which is connected to a single photodetector 14.

Light sources Pl-Pn are sequentially driven with a drive circuit 16 under the control of a computer 15 in such a periodic way that the operational timing of one light source is out of phase with that of another. The outputs of the photodetector 14 are read in synchronism with the drive timing of pulse light sources Pl-Pn and supplied to an integrator 18 through an amplifier 17. The integrated outputs are subjected to analog-to-digital conversion in an A/D converter 19 and stored in the computer 15 as detection data to which assigned are addresses corresponding to the respective numbers of the pulse light sources Pl-Pn.

With the constitution described above, the light sources Pl-Pn are sequentially driven as shown in FIG.

Figure 4:
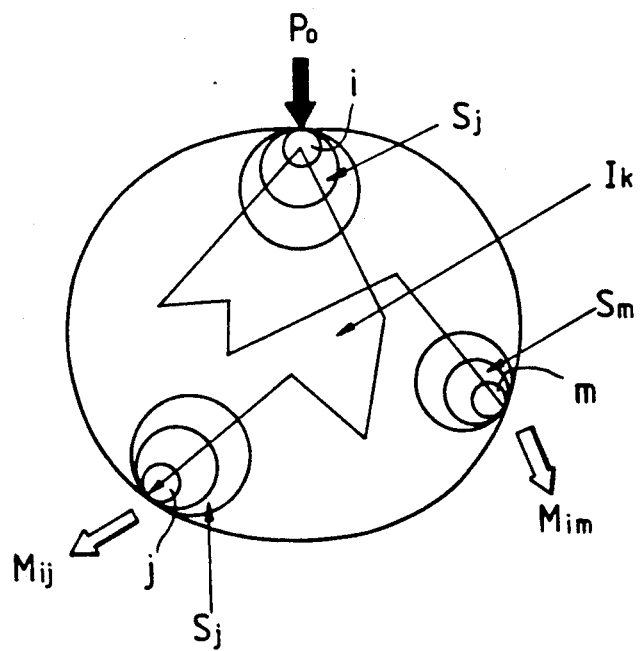
FIG. 4 is a diagram showing the light path launched into the head.

3 to launch light beams into the head 13 through launching fibers 11-$l$ to 11-$n$. For instance, a light source Pi is driven to have light launched into the head 13 through a launching fiber 11-$i$. As shown in FIG. 4, the incident light is scattered and its direction becomes random as it goes deeper into the head and travels away from the incident site i. Therefore, the absorption information to be obtained from the head 13 is chiefly determined by the absorption information in the vicinity of the incident site i and that in the vicinity of the output site, and the absorption information in the remaining whole part of the head 13 merely contributes as an averaged manner. In other words, optical outputs $M_{ij}$ and $M_{im}$ from respective output sites j and m are expressed as follows:

$$M_{ij} = P_o S_i (\Sigma I_k) S_j$$

$$M_{im} = P_o S_i (\Sigma I_k) S_m \qquad (1)$$

where
- $P_o$: the intensity of light launched into the incident site i;
- $S_i$: the light transmittance in the vicinity of the incident site i;
- $I_k$: the light transmittance in the internal part of the head 13 (e.g., site k);
- $S_j$: the light transmittance in the vicinity of the output site j; and
- $S_m$: the light transmittance in the vicinity of the output site m.

It is assumed in obtaining equation (1) that in the process of light travel to the output sites j and m the light transmittance in the internal part of the head 13 is averaged as expressed by $\Sigma I_k$ and the same value of light transmittance is picked up from any output site.

The optical outputs $M_{il}$ to $M_{im}$ from all output sites are supplied to the single photodetector 14 through associated pickup fibers 12-$l$ to 12-$m$ and added together to produce:

$$M_i = \sum_{j=1}^{m} M_{ij} = P_o S_i (\Sigma I_k)(\Sigma S_j). \qquad (2)$$

As one can see from equation (2), the light transmittance values of individual output sites are averaged by summing up outputs $M_{il}$ to $M_{im}$ and as a consequence, a parameter that is proportional to the transmittance $S_i$ at incident site i can be detected by the photodetector 14. Light from pulse light source $P_i$ is cyclically launched into the head 13 at the incident site i, and the transmittance $S_i$ at the incident site i that is detected with the photodetector 14 at each time of light launching is sent to the integrator 18 via the amplifier 17 to be integrated at prescribed times. The integrated transmittance $S_i$ is subjected to analog-to-digital conversion in the A/D converter 19 and stored in the computer 15 as detection data corresponding to the pulse light source $P_i$.

Pulse light sources other than $P_i$ are sequentially driven and similar operations are performed to determine the light transmittance values of incident sites other than i as detection data that correspond to the respective driven pulse light sources. The detection data thus obtained are processed by predetermined procedures to determine the time-dependent change in the transmittance, that is, the light absorption at a plurality of local sites, that is, the incidence sites in the brain.

Figure 5:
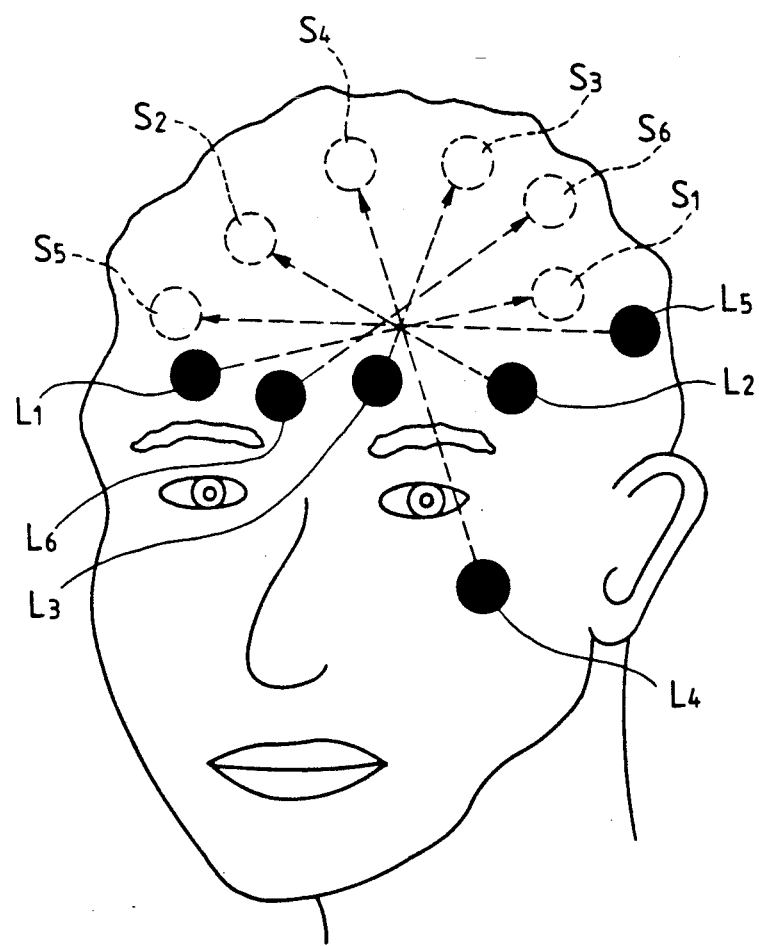
FIG. 5 is a diagram showing an application of a prior art examination apparatus.

In the prior art examination apparatus shown in FIG. 5, a light launching fiber is located in one-to-one correspondence to a light pickup fiber and the light absorption on the straight line in the brain that connects these fibers is detected as the necessary information. This is not the case in the embodiment of the present invention described above, in which scattered light beams resulting from the launching of light at a selected incident site i is picked up simultaneously from all of the output sites and the outputs thus picked up are added together as mathematical processing. This offers the advantage that even if the intensity of incident light $P_o$ launched at the site i is not very high, the absorption of light at the local incident site i can be detected with high sensitivity. As a further advantage, any variation that might occur in the result of detection as a consequence of slight changes in the position or direction in which the light launching fibers 11-$l$ to 11-$n$ and the pickup fibers 12-$l$ to 12-$m$ are attached can be prevented effectively in the apparatus of the present invention.

In the embodiment described above, scattered light beams from a plurality of output sites are sent to the single photodetector 14 where the individual outputs are added together. Alternatively, a plurality of photodetectors that correspond to the respective pickup fibers 12-$l$ to 12-$m$ may be provided in such a way that the outputs of the photodetectors are added together in the computer 15.

The examination apparatus shown in FIG. 1 may be modified in such a way that a plurality of light sources that emit light beams of different wavelengths are employed and that comparison is made between the intensities of outputs that correspond to the respective wavelengths. In this way, the differences in absorption spectra inherent in such substances as oxygen and glucose in the brain are utilized to achieve high-speed measurements of the spatial distribution and temporal change of a particular substance in the brain (cerebral cortex).

The foregoing embodiment concerns examination of a certain abnormality in the brain. It should be noted that the apparatus of the present invention may be applied for diagnostic purposes to other organs of a human or animal body, as well as ordinary objects to be measured such as a piece of flesh.

As described on the foregoing pages, the apparatus of the present invention is adapted to detect light absorption at a local site in an object of interest by performing mathematical processing on the intensities of scattered light beams picked up from a plurality of sites in the object. Therefore, this apparatus enables light absorption at a local site in the object to be detected with high sensitivity even if the intensity of incident light is not very strong. As a further advantage, the apparatus provides highly precise results of detection without being greatly influenced by a deviation in the position or direction in which a fixture such as an optical fiber is attached to the object to be measured.

What is claimed is:

1. An examination apparatus for examining an object composed of tissue employing transmission photometry, comprising:
   light launching means for successively launching an incidence light beam to said object composed of tissue, said incidence light beam having a predetermined wavelength, and said light launching means comprising means for cyclically launching incidence light beams to said object at a plurality of incidence sites;

means, comprising a plurality of light-receiving means positioned at least adjacent a plurality of output sites, for picking up, in synchronism with each successive launching of said incidence light beam, light beams of said predetermined wavelength scattered in said object from said plurality of output sites as light intensity data, and for performing mathematical processing on said light intensity data for each successive launching of said incidence light beam to obtain absorption data representing a light absorption quantity at said incidence site;

wherein said means for picking up light beams and for mathematical processing picks up, in synchronism with each launching of said incidence light beam at any incidence site, said light beams scattered in said object from said plurality of output sites as said light intensity data, and performs said mathematical processing on said light intensity data for each launching of said incidence light beam at any incidence site to obtain total absorption data representing light absorption quantities at said plurality of incidence sites; and wherein said means for performing mathematical processing adds said light intensity data picked up from said plurality of output sites.

2. An examination apparatus according to claim 1, wherein said means for picking up light beams and for performing mathematical processing comprises a single photodetector which adds said light intensity data.

3. An examination apparatus according to claim 2, wherein said means for picking up light beams and for mathematical processing further comprises an integrator for integrating outputs of said photodetector at predetermined times of launching of said incidence light beam.

4. An examination apparatus according to claim 1, wherein said means for picking up light beams and for mathematical processing comprises:
a plurality of photodetectors for detecting said respective light beams scattered in said object to produce said light intensity; and
computing means for adding said light intensity data.

5. An examination apparatus according to claim 1, wherein said means for picking up light beams and performing mathematical processing adds said light intensity data from each launching of said incidence light beam to obtain said absorption data and integrates said absorption data from launching said incidence light beams at each of said plurality of incidence sites to obtain said total absorption data.

6. An examination apparatus according to claim 1, wherein said light launching means is for launching an incidence light beam of a second wavelength for each launching of said incidence light beam of said predetermined wavelength and said means for picking up light beams of said predetermined wavelength and for mathematical processing further comprises means for picking up said light beams of said second wavelength scattered in said object from said plurality of output sites as second light intensity data, and for performing mathematical processing on said second light intensity data for each launching of said incident light beam of said second wavelength to obtain second absorption data representing a second light absorption quantity at said incidence site.

7. An examination apparatus according to claim 1, wherein said means for performing mathematical processing by adding calculates $M_i$ where said light intensity data at an output site j is represented as $M_{ij}$;

said absorption data at said incidence site i is represented as $M_i$; and $$M_i = \sum_{j=1}^{m} M_{ij}$$
$$= P_o S_i (\Sigma I_k)(\Sigma S_j)$$

wherein there are m output sites; and $P_o$: the intensity of light launched into the incident site i;

$S_i$: the light transmittance in the vicinity of the incident site i;

$I_k$: the light transmittance in an internal part of the object; and $S_j$: the light transmittance in the vicinity of the output site j where j is a number from one to m.

* * * * *